United States Patent [19]

Sutton et al.

[11] Patent Number: 5,714,340
[45] Date of Patent: Feb. 3, 1998

[54] IMMUNOASSAY ELEMENTS HAVING A RECEPTOR ZONE

[75] Inventors: Richard Calvin Sutton, Rochester; Margaret Jeanette Smith-Lewis, Pittsford; Linda Ann Mauck, Rochester; Wayne Arthur Bowman, Walworth; Susan Jean Danielson, Rochester, all of N.Y.

[73] Assignee: Johnson & Johnson Clinical Diagnostics, Inc., Rochester, N.Y.

[21] Appl. No.: 260,939

[22] Filed: Jun. 16, 1994

Related U.S. Application Data

[63] Continuation-in-part of Ser. No. 994,857, Dec. 22, 1992, abandoned, and Ser. No. 994,858, Dec. 22, 1992, abandoned.

[51] Int. Cl.$^6$ .................. G01N 33/53; G01N 33/543; G01N 33/545
[52] U.S. Cl. .................. 435/7.92; 422/56; 422/57; 435/7.93; 435/287.1; 435/287.2; 435/287.7; 435/287.8; 435/287.9; 435/810; 436/169; 436/170; 436/518; 436/528; 436/529; 436/531; 436/532; 436/533; 436/534; 436/810
[58] Field of Search .................. 422/55–58; 436/518, 436/528, 529, 531, 532–534, 169, 170, 810; 435/7.92, 7.93, 810, 287.1, 287.2, 287.7, 287.8, 287.9

[56] References Cited

U.S. PATENT DOCUMENTS

| | | | |
|---|---|---|---|
| 4,089,747 | 5/1978 | Bruschi | 435/28 |
| 4,258,001 | 3/1981 | Pierce et al. | 422/56 |
| 4,430,436 | 2/1984 | Koyama et al. | 436/53 |
| 4,517,288 | 5/1985 | Giegel et al. | 435/7.9 |
| 4,668,619 | 5/1987 | Greenquist et al. | 435/7.9 |
| 4,670,381 | 6/1987 | Frickey et al. | 435/7.9 |
| 4,670,385 | 6/1987 | Babb et al. | 435/28 |
| 4,828,983 | 5/1989 | McClune | 435/28 |
| 4,870,007 | 9/1989 | Smith-Lewis | 435/28 |
| 4,874,692 | 10/1989 | Elkenberry | 435/7 |
| 4,959,305 | 9/1990 | Woodrum | 422/56 |
| 4,966,856 | 10/1990 | Ito et al. | 436/170 |
| 5,094,962 | 3/1992 | Snyder et al. | 436/518 |
| 5,155,166 | 10/1992 | Danielson et al. | 525/54.1 |

FOREIGN PATENT DOCUMENTS

| | | |
|---|---|---|
| 1240445 | 8/1988 | Canada. |
| 0 238 012 A2 | 9/1987 | European Pat. Off.. |
| 0 308 235 B1 | 3/1989 | European Pat. Off.. |

OTHER PUBLICATIONS

Statistics for Experimenters. An Introduction to Design, Data Anlysis, and Model Building by Hunter et al., John Wiley & Sons, N.Y., N.Y. (1978).

*Primary Examiner*—Christopher L. Chin
*Attorney, Agent, or Firm*—Alan J. Morrison

[57] ABSTRACT

A dry immunoassay analytical element, for assaying a ligand is disclosed. The element comprises, in the following order, (a) a layer containing a labeled ligand, (b) a bead spreading layer, c) a cross-linked hydrophilic polymer layer and d) a support; wherein (i) a fixed concentration of an immobilized receptor for the labeled ligand is located in a zone at the interface of layers (b) and (c); and (ii) the receptors are immobilized by being covalently bonded to polymeric beads that are smaller than the beads in layer (c).

16 Claims, 5 Drawing Sheets

FIG. 7 ns in a ce with an applied to the element. After a a substrate for the labeled ligand r. The reaction with substrate

IMMUNOASSAY ELEMENTS HAVING A RECEPTOR ZONE

CROSS-REFERENCE TO THE RELATED APPLICATIONS

This is a continuation-in-part of application Ser. Nos. 07/994,857 and 07/994,858, both filed Dec. 22, 1992 and both now, abandoned.

FIELD OF THE INVENTION

This invention relates to an immunoassay element, a method for making the element, and use thereof in an immunoassay.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes include, for example, antigens, antibodies, therapeutic drugs, narcotics, enzymes, hormones, proteins, etc.

The analyte, which is the target of the assay is referred to herein as the ligand, and the labeled analyte is referred to as the labeled ligand (including immunocompetent derivatives and analogs of such ligand). Compounds which specifically recognize the ligand and the labeled ligand and react to form complexes with them are referred to herein as receptors. The receptor and the ligand or labeled ligand form a conjugate pair. Any member of the pair can function as a receptor or a ligand.

In competitive binding immunoassays, a labeled ligand is placed in competition with unlabeled ligand for reaction with a fixed amount of the appropriate receptor. Unknown concentrations of the ligand can be determined from the measured signal of either the bound or unbound (i.e. free) labeled ligand. The reaction proceeds as follows:

ligand+labeled ligand+receptor<=>ligand-receptor+labeled ligand-receptor.

Immunoassay analytical elements are known. In general such elements comprise receptors, such as antibodies for a ligand, immobilized in a particulate layer. In addition the element usually contains a reagent system that through interaction with a bound or unbound species results in a signal that can be correlated to the concentration of ligand in a sample. In use the sample is manually combined with an enzyme labeled ligand and applied to the element. After a time a solution containing a substrate for the labeled ligand is applied to the particulate layer. The reaction with substrate is catalyzed by the enzyme label to form a reaction product that ultimately causes a signal color to develop. The reflection density of the color can be correlated to the concentration of the ligand in the sample. Similar signal development systems are known for other known conventional labels such as radioactive tags, chromophores, fluorophores, stable free radicals, and enzyme cofactors, inhibitors and allosteric effectors.

Frequently the above analytical elements are used in highly automated immunoassays. The need to add labeled ligand to the sample before conducting the assay reduces the potential output of automated systems.

U.S. Pat. Nos. 4,517,288 and 4,258,001 and EPA 0238012 suggest use of a labeled ligand coated over the particulate layer in which the receptor is immobilized. U.S. Pat. No. 4,517,288 teaches using a barrier layer between the labeled ligand layer and the particulate layer in order to avoid prereaction between the receptor and the labeled ligand. EPA 0238012 suggests that a laminate of the two layers should be prepared under dried conditions and stored as a dry sheet until the commencement of the assay to avoid prebinding.

The problem is that neither of these patent publications teaches one skilled in the art how to make an immunoassay element that avoids (a) inactivation (low sensitivity) of receptors, such as antibodies, and (b) deleterious prebinding between the labeled ligand and the receptor which prevent completion of an immunoassay within a commercially reasonable time (up to 10 minutes).

SUMMARY OF THE INVENTION

The objective of the present invention is to overcome the need to add labeled ligand to the sample or element during the actual assay procedure without adversely affecting the capacity of the receptor to be useful in an immunoassay element.

This objective is accomplished with the present invention which provides a dry immunoassay analytical element, for assaying a ligand, comprising in the following order, (a) a layer containing a labeled ligand, (b) a bead spreading layer, c) a cross-linked hydrophilic polymer layer and d) a support; wherein (i) a fixed concentration of an immobilized receptor for the labeled ligand is located in a zone (receptor zone) at the interface of layers (b) and (c); and (ii) the receptors are immobilized by being covalently bonded to polymeric beads that are smaller than the beads in layer (b).

The immunoassay element of this invention is substantially free of prebinding in that the rate of change of transmission density (Dt) of an immunoassay carried out on such an element is substantially the same as the rate of change of transmission density (Dt) obtained with the same element except that the labeled ligand is not coated in the element. Instead the labeled ligand is applied to the element, concurrently with the sample to be tested.

The element exhibits good sensitivity compared to other elements having the receptors in the bead spreading layer (b) or that have the receptor zone coated with polymer that are different from those used in the present invention.

The present invention also provides a method for the assay of immunologically reactive ligand in an aqueous liquid sample. The method comprises the steps of:

A. providing a dry immunoassay analytical element according to the present invention wherein the labeled ligand is an enzyme labeled ligand;

B. contacting a finite area of the layer comprising the enzyme labeled ligand with a sample of the liquid sample thereby forming at least one of (i) an immobilized ligand-receptor complex and (ii) an immobilized enzyme labeled ligand-receptor complex;

C. contacting the finite area of the layer comprising the enzyme labeled ligand with a substrate solution thereby catalyzing the development of a color; and D. determining the concentration of the ligand colorimetrically.

The present invention further provides a method of making an immunoassay element that eliminates significant prebinding, between a coated labeled ligand and a receptor for the ligand, before a sample is applied to the element. The method comprises the steps of:

A. coating a layer of a cross-linked hydrophilic polymer on a support;

B. coating a composition over the layer formed in step A to form a zone; wherein the composition comprises (i) a receptor covalently bonded to polymeric beads having a diameter in the range of 0.1 to 5 μm ii) dispersed in a polymer selected from the group consisting of (I), (II), (III), (IV), (V) and (VI) described hereinafter under details of the invention.

C. coating a bead spreading layer over the receptor zone; and

D. coating a layer containing an enzyme labeled ligand over the bead spreading layer; wherein each coating is allowed to dry before being overcoated. According to the present invention the element prepared according to this method may have a receptor zone that is free of some or essentially all of the polymer used to coat the receptor zone.

BRIEF DESCRIPTION OF FIGURES

FIGS. 1–7 are photomicrographs showing different views of elements of the invention.

DETAILED DESCRIPTION OF THE INVENTION

The elements of this invention comprise a support (d) bearing a layer of a cross-linked hydrophilic layer (c). The immobilized receptor is coated over layer (c) in a polymer according to the invention, to form the receptor zone. The bead spreading layer (b) is coated over the receptor zone. The labeled ligand layer (a) is coated over the bead spreading layer.

The element can include additional layers such as those described infra. All of such layers, except the labeled ligand coating, can be coated using coating techniques known in this art and which are briefly described infra.

Preferably the labeled ligand is gravure coated to 1) minimize wet coverage of the labeled ligand coating composition, to avoid precontact of the labeled ligand with the receptor, while at the same time maintaining enough wetness to achieve uniform coverage of the labeled ligand and 2) and achieve rapid drying in a way that a) removes substantially all of the coating solvent; b) avoids adversely affecting the porosity of the spread layer and spreading time and c) maintains sufficient enzyme activity.

The relative affinity of antibody and labeled ligand for each other is also an important factor in minimizing prebinding. This factor is controlled, as is well known by those skilled in this art, by manipulating the structure of the labeled ligand together with a prudent choice of antibody.

In general the level of coated labeled ligand coverage needed in an element is determined empirically for each specific immunoassay according to the following procedure:

1. Determine the concentration of labeled ligand needed to achieve acceptable immunoassay performance when the immunoassay is performed by contacting the analytical element with the labeled ligand concurrently with a sample. Acceptable assay performance is achieved when (a) the assay can be carried out in less than 20 minutes; (b) the dynamic range of the assay is such that the minimum and maximum ligand concentrations detectable cover a clinically useful concentration range; and (c) clinically significant ligand concentrations can be detected across the dynamic range.

2. Empirically determine the level of coated labeled ligand coverage needed with the same analytical element to achieve the above established acceptable assay performance by:

A. Coating, directly over the particulate receptor zone of the element used to establish optimum spotted labeled ligand levels, the labeled ligand at a coverage in $g/m^2$ that is some fraction, multiple or the same as the concentration of labeled ligand used in spotting the labeled ligand in 1, supra.

B. Conduct a series of assays with test samples containing a known concentration of the ligand.

C. Compare the results of the assays with the known concentration of ligand; and D. Repeat steps B and C as needed, varying the labeled ligand coverage according to the results seen in step 2C to determine the labeled ligand coverage required.

Depending on the labeled ligand, the coverage of the labeled ligand could be less than, the same or several multiples greater (2×, 3×, 4×, etc.) than the labeled ligand concentration needed when the same assay is carried out by spotting the labeled ligand directly on the analytical element.

Using the above guidelines, carefully controlled gravure coating procedures were successfully carried out using the following coverages and drying protocols. The labeled ligand coatings in the elements of the invention were prepared with a gravure machine (made by Yasui of Japan). Drying conditions are generally about 120° F. (49° C.) in the first drying section only. The second section was not used. A typical gravure cylinder used contained 295 cells/inch ($1.344 \times 10^8$ cells/$m^2$). The cells had a depth of 19 microns, a width of 72 microns and a land width between cells of 12 microns. This cylinder will deliver about 4.3 $g/m^2$ of coating composition containing the labeled ligand to the bead spreading layer using the direct gravure process at a coating machine speed of 50 ft/min (15.24 m/minute). Other gravure cylinders can deliver from about 2.5 to 6.8 $g/m^2$ of coating solution. Those skilled in the gravure coating arts will be readily able to adapt the previously described procedure to any gravure coating machine. The coating composition for the labeled ligand was as follows:

| Coated Labeled Ligand Coating Composition Based on 4.3 $g/m^2$ Wet Coverage | |
|---|---|
| Component | $g/m^2$ Dry Coverage |
| MOPS Buffer | .0045 |
| BSA (Bovine Serum Albumin) | .000215 |
| poly(acrylamide) | .00108 |
| 4'-Hydroxyacetanilide | .000325 |
| *Labeled ligand | .000016 |
| *Labeled ligand has been coated anywhere between 4 and 64 μg/$m^2$ | |

The remaining layers of the element can be coated using well known coating techniques in this art. However each layer is coated separately and allowed to dry before application of subsequent layers.

The bead spreading layer is porous and coated over the receptor zone. Materials for use in such layers are well known in the art of making dry analytical elements as disclosed, for example, in U.S. Pat. No. 4,258,001. Such layers include macroporous layers made from cloth, paper, etc. This layer can be easily constructed to have suitable porosity for use in the elements of the present invention to accommodate a test sample (e.g. 1 to 100 μL), diluted or undiluted. Preferably, the spreading layer is isotropically porous, which property is created by interconnected spaces between the particles comprising the zone. By isotropically porous is meant that the spreading layer uniformly spreads the applied fluid radially throughout the layer.

Useful bead spreading layers are disclosed in U.S. Pat. Nos. 4,670,381; 4,258,001 and 4,430,436. Particularly useful spreading layers are those having a particulate structure formed by organo-polymeric particles and a polymeric adhesive for those particles described in U.S. Pat. No. 4,258,001. The organo-polymeric particles useful in the spreading layer are generally heat-stable, spherical beads having a particle size in the range of from about 10 to 40 μm, preferably 20 to 35 μm in diameter or even smaller. However such beads are always larger than the beads used in the receptor zone to immobilize the receptor.

The particles can be composed of a wide variety of organic polymers, including both natural and synthetic polymers, having the requisite properties. Preferably, however, they are composed of one or more addition polymers described in the aforementioned patents.

The receptor zone is prepared and coated over the cross-linked hydrophilic layer. The receptors are covalently bonded to polymer particles through surface reactive groups on the receptor (nucleophilic free amino groups and sulfhydryl groups). The polymer particles are generally beads having a diameter of 0.1 to 5 μm.

A general procedure for attaching receptors to the small polymer beads includes covalently attaching the selected receptor to the beads using generally known reactions. With many pendant groups for example the haloalkyl, 2-substituted activated ethylsulfonyl and vinylsulfonyl, the receptor can be directly attached to the beads. Generally, the beads are mixed with the receptor in an aqueous buffered solution (pH generally from about 5 to about 10) and a concentration of from about 0.1 to about 40 weight percent polymer particles (preferably from about 0.1 to about 10 weight percent). The amount of receptor is at a ratio to polymer of from about 0.1:1000 to about 1:10, and preferably from about 1:100 to about 1:10. Mixing is carried out at a temperature in the range of from about 5° to about 50° C., and preferably at from about 5° to about 40° C., for from about 0.5 to about 48 hours. Any suitable buffer can be used.

In some instances, the pendant reactive groups on the outer surface must be modified or activated in order to cause covalent attachment of the ligand. For example, carboxyl groups must be activated using known carbodiimide or carbamoylonium chemistry, described in EP 308235 published 22 Jul. 1992 and U.S. Pat. No. 5,155,166.

The attachment of the receptor to carboxyl group-containing monodispersed polymer beads, however, is carried out in two steps, the first of which involves contacting an aqueous suspension of the particles with a carbodiimide or a carbamoylonium compound to produce reactive intermediate polymer particles having intermediate reactive groups in place of the carboxyl groups. This step is carried out at a suitable pH using suitable acids or buffers to provide the desired pH. Generally, the pH is less than 6, but this is not critical as long as the reaction can proceed. More likely, the pH is between about 3.5 and about 7. The molar ratio of carbodiimide or carbamoylonium compound to the carboxyl groups on the surface of the particles is from about 10:1 to 500:1.

In the second step of the method, the reactive intermediate formed in the first step is contacted with a reactive amine- or sulfhydryl-group containing receptor. A covalent linkage is thereby formed between the particles and the receptor. The weight ratio of the receptor to the polymeric particles is generally from about 1:1000 to about 1:1, and preferably from about 1:100 to about 1:10.

In other instances, an epoxy group on the outer surface can be hydrolyzed to form a diol compound capable of reacting with cyanogen bromide which can act as a coupling agent for amine groups in the immunological species. Aldehydes can react directly with amines to form a Schiff's base which can be subsequently reduced to form a covalent link. Alternatively, the aldehyde can be oxidized to an acid and chemistry identified above for carboxyl groups can be used to form an amide linkage.

Any reactive amine- or sulfhydryl-containing receptor can be attached to the polymeric beads as long as that receptor contains a reactive amine or sulfhydryl group, respectively which will react with the reactive groups on the polymer or with the intermediate formed by the reaction of a carbodiimide or a carbamoylonium compound with carboxyl groups on the particles in the case which the polymer has reactive carboxyl groups.

The small polymer beads having reactive groups that readily react directly with the amine or sulfhydryl groups on the receptors are simply mixed with the receptors, in an appropriate buffer if necessary, and allowed to react.

Polymers from which beads for the receptor can be selected include the following: poly(m & p-chloromethylstyrene), poly(styrene-co-m & p-chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[m & p-(2-chloroethylsulfonylmethyl)phenyl]acrylamide} (99.3:0.7 molar ratio), poly(m & p-chloromethylstyrene-co-methacrylic acid) (95:5, 98:2 and 99.8:0.2 molar ratio), poly(styrene-co-m & p-chloroethylsulfonylmethylstyrene-co-methacrylic acid) (93.5:4.5:2 molar ratio), poly{styrene-co-N-[m & p-(2-chloroethylsulfonylmethyl)phenyl]acrylamide-co-methacrylic acid} (97.3:0.7:2 molar ratio), poly(styrene-co-m & p-chloromethylstyrene) (70:30 molar ratio), poly[styrene-co-3-(p-vinylbenzylthio)propionic acid] (97.6/2.4 molar ratio), poly(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m & p-divinylbenzene) (89:10:1 molar ratio), poly(styrene-co-2-carboxyethyl acrylate) (90:10 molar ratio), poly(methyl methacrylate-co-acrylic acid) (70:30 molar ratio), poly(styrene-co-m & p-vinylbenzaldehyde) (95:5 molar ratio), and poly(styrene-co-m- and p-vinylbenzaldehyde-co-methacrylic acid) (93:5:2 molar ratio).

The receptor zone must be coated with a polymer selected from group consisting of (I), (II), (III), (IV), (V) and (VI) as follows:

(I) cross-linked polymers comprising about 30 to 97 weight percent of polymerized N-alkyl-substituted acrylamide monomers, about 3 to 25 weight percent polymerized crosslinking monomer having at least two addition polymerizable groups per molecule of crosslinking monomer, and 0 to 60 weight percent of other polymerized hydrophilic monomers (II) poly(vinyl alcohol);

(III) bovine serum albumin;

(IV) acacia gum;

(V) homopolymers of poly-N-vinylpyrrolidone having a molecular weight in the range 8000 to 400,000; and (VI) water-soluble vinyl addition copolymers having two or more monomers selected from the group consisting of acrylamide, methacrylamide, N-alkylsubstituted acrylamides, N-alkyl substituted methacrylamides, 1-vinylimidazole, 2-alkyl substituted-1-vinylimidazoles, 2-hydroxyalkyl substituted-1-vinylimidazoles, N-vinylpyrrolidone, hydroxyalkyl acrylates, hydroxyalkyl methacrylates, acrylic acid, sulfoalkyl acrylates, sulfatoalkyl acrylates, sulfoalkyl methacrylates, sulfatoalkyl methacrylates, N-sulfoalkylacrylamides, N-sulfatoalkylacrylamides, and N-sulfoalkylmethacrylamides, N-sulfatoalkylmethacrylamides, ethylenesulfonic acid and sulfo-substituted styrenes. The alkali metal (sodium, lithium, and potassium), and ammonium salts of the monomers containing sulfato- and sulfo- moieties are included in group (VI). Alkyl, wherever it appears in group (I) and (VI) monomers include 1 to 6 carbon atoms.

The receptor zone must be coated with a polymer according to the group (I), (II), (III), (IV), (V) and (VI). However the zone in the finished element may be essentially free of the polymer. Some, none, or essentially all, of the polymer will migrate into the bead spreading layer (b) when layer (b) is coated over the receptor zone coating.

Many polymers tested for coating, such as those disclosed in U.S. Pat. No. 4,517,288 by Pierce et al, were not operative. Coating without polymer also resulted in an inoperative element. The polymers used herein do not adversely affect the binding activity of antibody receptors.

Further some of the polymers of group (I) herein make it possible to form uniform coatings of receptor zones due to the very low viscosities achieved from sheer thinning during extrusion hopper coating. A further advantage is achieved with certain of the polymers in that, immediately after forming uniform coatings, the viscosity of the polymers increases substantially resulting in a "set layer" that remains stable and uniform during wet transport and drying of the polymers.

Useful N-alkyl-substituted acrylamides for groups (I) and (IV) polymers include N-isopropylacrylamide, N-n-butylacrylamide, N,N-diethylacrylamide and N-n-propylacrylamide. This includes cross-linked polymers comprising from about 30 to 97 weight percent of a polymerized N-alkyl substituted acrylamide such as N-isopropylacrylamide. Polymers comprising 60 to 97 weight percent of polymerized N-isopropylacrylamide are used in the examples to clarify the utility of group (I) polymers.

Group (I) polymers also comprise from about 3 to 25 weight percent of one or more polymerized crosslinking monomers having at least two addition-polymerizable groups per molecule. These crosslinking monomers are generally well known in the art. The preferred crosslinking monomers contain acrylamido or methacrylamido groups to facilitate polymerization with the N-alkyl-substituted acrylamides.

Examples of useful crosslinking monomers for group (I) polymers are:

N,N'-methylenebisacrylamide;
N,N'-methylenebismethacrylamide;
ethylene dimethacrylate;
2,2-dimethyl-1,3-propylene diacrylate;
divinylbenzene;
mono[2,3-bis(methacryloyloxy)propyl] phosphate;
N,N'-bis(methacryloyl)urea;
triallyl cyanurate;
allyl acrylate;
allyl methacrylate;
N-allylmethacrylamide;
4,4'-isopropylidenediphenylene diacrylate;
1,3-butylene diacrylate;
1,4-cyclohexylenedimethylene dimethacrylate;
2,2'-oxydiethylene dimethacrylate;
divinyloxymethane;
ethylene diacrylate;
ethylidene diacrylate;
propylidene dimethacrylate;
1,6-diacrylamidohexane;
1,6-hexamethylene diacrylate;
1,6-hexamethylene dimethacrylate;
phenylethylene dimethacrylate;
tetramethylene dimethacrylate;
2,2,2-trichloroethylidene dimethacrylate;
ethylenebis(oxyethylene) diacrylate;
ethylenebis(oxyethylene) dimethacrylate;
ethylidyne trimethacrylate;
propylidyne triacrylate;
vinyl allyloxyacetate;
1-vinyloxy-2-allyloxyethane;
2-crotonoyloxyethyl methacrylate;
diallyl phthalate; and
2-(5-phenyl-2,4-pentadienoyloxy)ethyl methacrylate.

The group (I) polymer can include 0 to 60 weight percent of polymerized hydrophilic monomers. Amounts of 5 to 35 weight percent are also useful. In particular such monomers have one or more groups selected from hydroxy, pyrrolidone, amine, amide, carboxy, sulfo, carboxylate salt, sulfonate salt and sulfate salt groups. Generally the counter ions of the salt groups are alkali metal or ammonium. Useful hydrophilic monomers are acrylic acid and methacrylic acid and their salts, sodium 2-acrylamido-2-methylpropane sulfonate, 2-hydroxyethyl acrylate, 2-hydroxyethyl methacrylate; 2-hydroxypropyl acrylate, 2-hydroxypropyl methacrylate; o- and p-styrenesulfonic acid, potassium salt; p-styrenesulfonic acid, potassium salt; p-styrenesulfonic acid, sodium salt; ethylenesulfonic acid, sodium salt; 2-sulfoethyl methacrylate, sodium salt; 2-sulfoethyl methacrylate, 3-acryloyloxypropane-1-sulfonic acid, sodium salt; 2-sulfobutyl methacrylate, sodium salt; 4-sulfobutyl methacrylate, sodium salt; N-(2-methacryloyloxy)ethylsulfate and glyceryl methacrylate.

Representative group (I) polymers include:

1. Poly(N-isopropylacrylamide-co-sodium 2-acrylamido-2-methylpropanesulfonate-co-N,N'-methylenebisacrylamide) (weight ratio 80/10/10).

2. Poly(N-isopropylacrylamide-co-methacrylic acid-co-N,N'-methylenebisacrylamide) (weight ratio 80/10/10).

3. Poly(N-isopropylacrylamide-co-2-hydroxyethyl methacrylate-co-N,N'-methylenebisacrylamide) (weight ratio 85/5/10).

4, 5, 6, 7, 8. Poly(N-isopropylacrylamide-co-2-hydroxyethyl methacrylate-co-sodium 2-acrylamido-2-methylpropanesulfonate-co-N,N'-methylenebisacrylamide) having the following weight ratios:

| Polymer | Weight Ratio |
| --- | --- |
| 4 | 80/5/5/10 |
| 5 | 83/5/2.5/9.5 |
| 6 | 84.5/5/0.5/10 |
| 7 | 83/5/2/10 |
| 8 | 80.9/4.8/4.8/9.5 |

It is an advantage of the group (I) polymers having the sulfonate salt groups that they have sufficient hydrophilicity so that they can be prepared without the presence of surfactants, which can be detrimental to the activity of the enzymes and/or antibodies coated in the assay elements. When surfactants are used in the polymerization process, they can be present from 0 up to about 9% of the polymerization mixture.

Representative monomers for forming the water-soluble vinyl addition copolymers of group (VI) are selected from the group consisting of 2-acrylamido-2-methylpropanesulfonic acid, sodium salt; o- and p-styrenesulfonic acid, potassium salt; p-styrenesulfonic acid, potassium salt; p-styrenesulfonic acid, sodium salt; ethylenesulfonic acid, sodium salt; 2-Sulfoethyl methacrylate, sodium salt; 2-sulfoethyl methacrylate; 3-acryloyloxypropane-1-sulfonic acid, sodium salt, 3-methacryloyloxypropane-1-sulfonic acid, sodium salt; 3-sulfobutyl methacrylate, sodium salt; 4-sulfobutyl methacrylate, sodium salt; N-(2-sulfo-1,1-dimethylethyl) acrylamide, potassium salt; and sodium 2-methacryloyloxyethylsulfate. Poly(N-isopropylacrylamide-co-sodium 2-acrylamido-2-methylpropanesulfonate) (weight ratio 85/15) are particularly useful.

The support can be any suitable dimensionally stable, and preferably, nonporous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc. The element can comprise one or more additional layers, e.g., separate or combined reagent/spreading layer and a gelatin/buffer layer containing other necessary additives such as electron transfer agents.

Other optional layers, e.g. subbing layers, radiation-blocking layers, etc. can be included if desired. All layers of the element are in fluid contact with each other, meaning that fluids and reagents and uncomplexed reaction products in the fluids can pass between superposed regions of adjacent layers.

The layers of the element can contain a variety of other desirable but optional components, including surfactants, thickeners, buffers, hardeners, antioxidants, electron transfer agents, coupler solvents, and other materials known in the art. The amounts of these components are also within the skill of a worker in the art.

Figure 1:
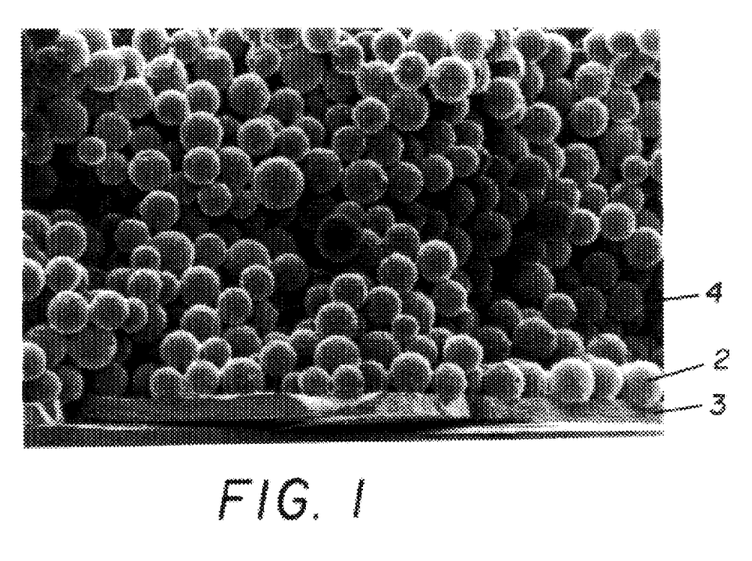
FIG. 1 is a cross section of a typical element.
Figure 2:
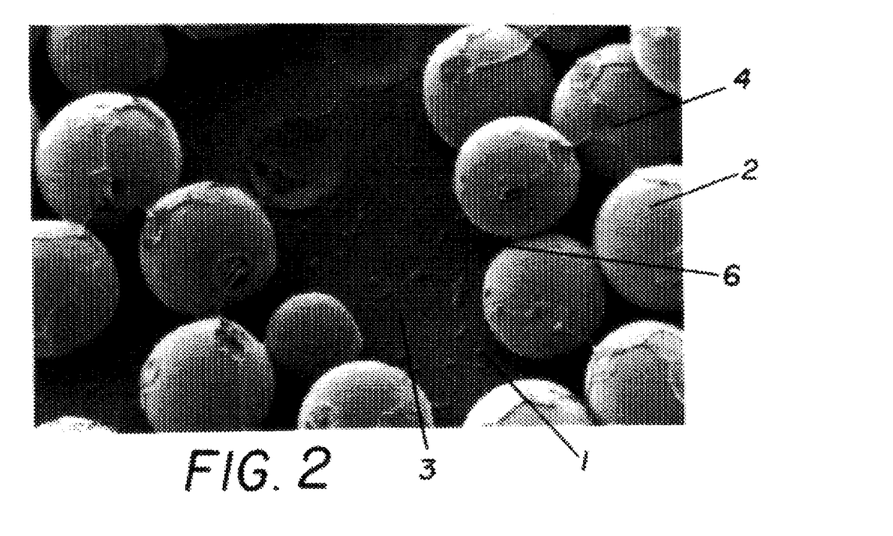
FIG. 2 is a normal incident view of the same element.
Figure 3:
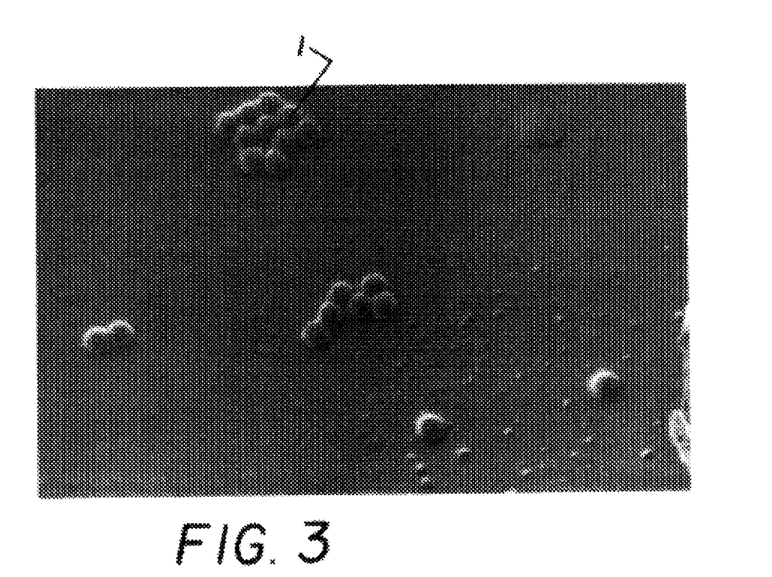
FIGS. 3 and 4 are the same view as FIG. 2 at greater magnification.
Figure 4:
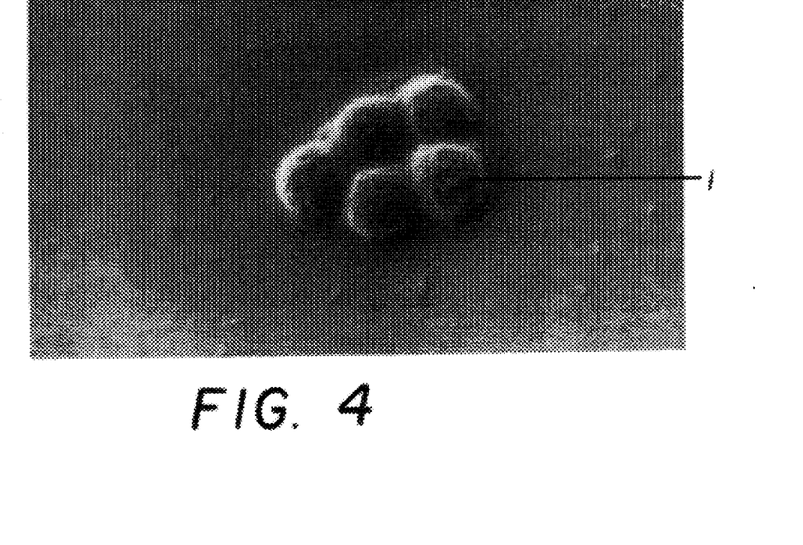
Figure 5:
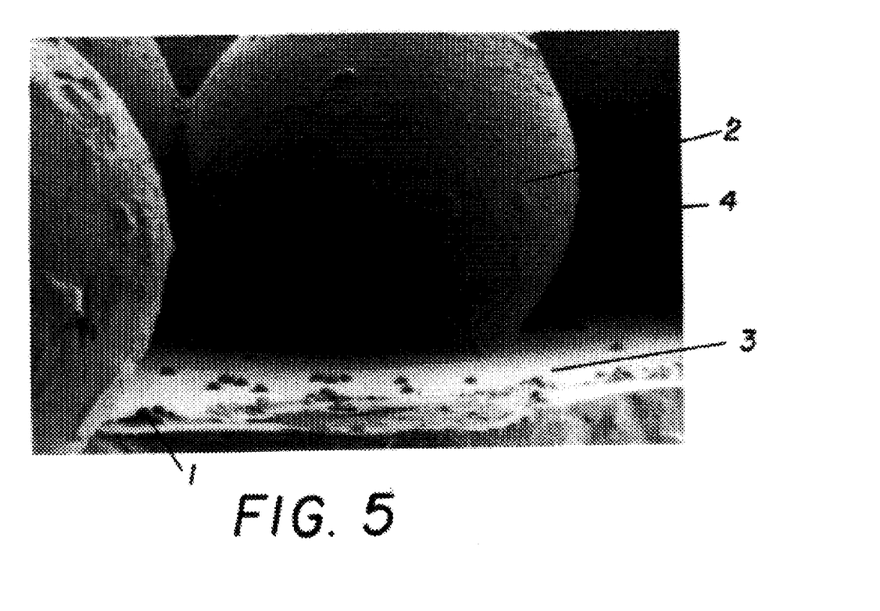
FIGS. 5 and 6 are cross-sections showing the bead spreading layer interfacing the cross-linked hydrophilic layer.
Figure 6:
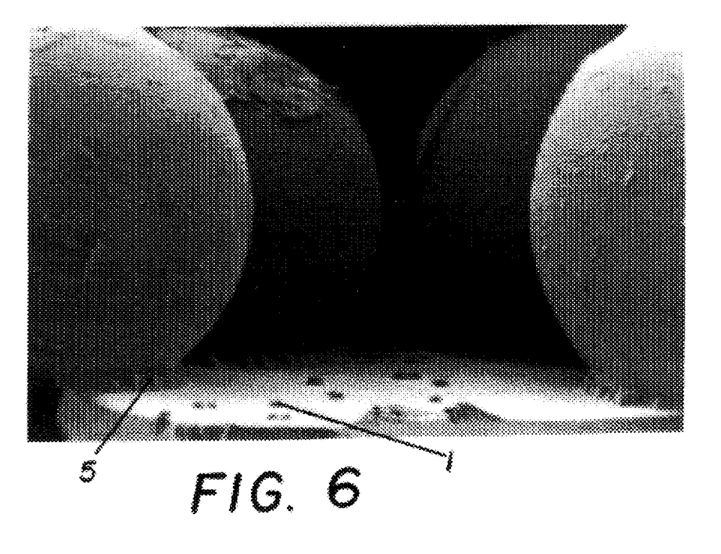
Figure 7:
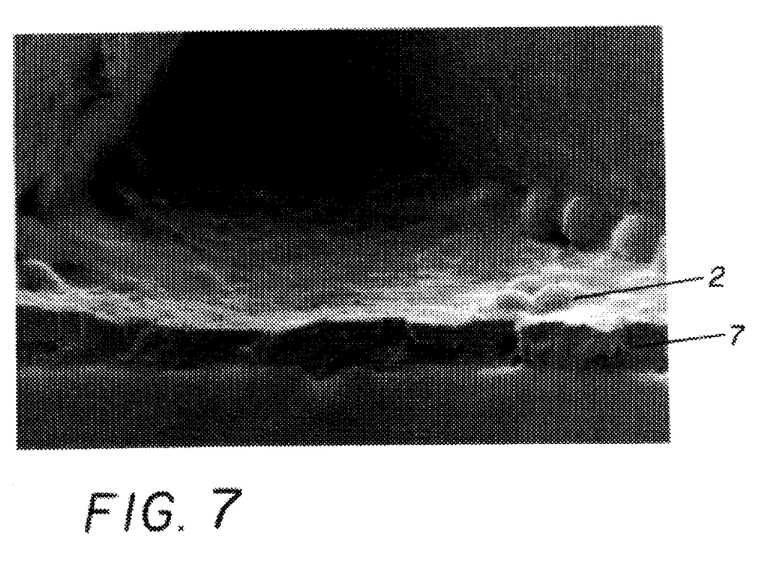
FIG. 7 is a cross section showing coated polymer in the receptor zone.

FIGS. 1–7 are photomicrographs of a typical element of the invention. FIG. 1 is a cross section of an element showing the bead spreading layer (4) in its entirety. It comprises a stack of beads (2) providing a bead spreading layer thickness of about 200 to 400 μm, usually about 300 μm. FIG. 1 also shows the cross-linked hydrophobic polymer layer (3). No receptor beads are seen in FIG. 1. FIG. 2 is a normal incidence view showing the receptor beads (1) upon which receptors are immobilized after most of the spreading layer beads (2) of the bead spreading layer (4) have been removed. The receptor beads (1) are shown in the receptor zone residing on the cross-linked hydrophilic polymer layer (3). FIG. 3 shows clusters of the receptor beads (1) at a greater magnification than FIG. 1. In FIG. 3 the clusters of receptor beads (1) do not contain visually detectable polymer. FIG. 4, more magnified than FIG. 2, shows a single cluster of receptor beads with visually detectable polymer. FIG. 5 is a cross-section showing a receptor bead (1) in the receptor zone interfacing with the cross-linked hydrophilic polymer layer (3) and a bottom portion of the bead spreading layer (4) containing a spreading layer bead (2). In FIG. 6, a receptor bead (1) is shown free of visually detectable polymer and with polymer (5) in the receptor zone. FIG. 7 shows a receptor zone (7) with coated polymer and receptor beads (1).

The elements can be used to determine low concentrations of immunologically reactive ligands in a liquid, such as a biological fluid (e.g., whole blood, serum, plasma, urine, spinal fluid, suspensions of human or animal tissue, feces, saliva, lymphatic fluid and the like). The ligands can be determined at concentrations as low as about $10^{-11}$ molar, and most generally at a concentration of from about $10^{-10}$ to about $10^{-4}$ molar.

Ligands which can be so determined, either quantitatively or qualitatively, include therapeutic drugs (e.g., phenobarbital, digoxin, digitoxin, theophylline, gentamicin, quinidine, phenytoin, propanolol, carbamazepine, tobramycin, lidocaine, procainamide and the like), natural or synthetic steroids (e.g., cortisol, aldosterone, testosterone, progesterone, estriol, etc.), hormones (e.g., thyroid hormones, peptide hormones, insulin, etc.), proteins (e.g. albumin, IgG, IgM, ferritin, blood clotting factors, C-reactive protein, isoenzymes, apolipoproteins, etc.), antigens, antibodies including monoclonal antibodies, and other species which will naturally react with a receptor. This invention is particularly useful for the determination of therapeutic drugs, such as digoxin, phenytoin, theophylline, or phenobarbital and hormones such as thyroxine or triiodothyronine.

The assay can be carried out using any enzyme label which can be attached to the ligand to form a labeled ligand. Enzymes, such as glucose oxidase, peroxidases such as horseradish peroxidase (HRP), alkaline phosphatase and galactosidase are preferred labels.

It is within the skill of the ordinary worker in clinical chemistry to determine a suitable substrate for a given label. The substrate can be a material which is directly acted upon by the enzyme label, or a material that is involved in a series of reactions which involve enzymatic reaction of the label. For example, if the enzyme label is a peroxidase, the substrate is hydrogen peroxide. Using glucose oxidase as an example, the substrate glucose is generally present in the reagent layer or added as a substrate solution to yield about 0.01 moles/$m^2$, and preferably from about 0.001 to about 0.1 mole/$m^2$. A worker skilled in the art would know how to adjust the amount of a particular substrate for the amount of enzyme label used in the assay.

The bead spreading layer or the receptor zone may contain an indicator composition comprising one or more reagents which provide a detectable species as a result of the reaction catalyzed by the label. The detectable species could develop a color, be radioactive, fluoresce, or be chemiluminescent. For present purposes the invention is illustrated using a colorimetric indicator composition which provides a colorimetrically detectable species as a result of enzymatic reaction of an enzyme-labeled ligand analog with a substrate.

The indicator composition can be a single compound which produces a detectable dye upon enzymatic reaction, or a combination of reagents which produce the dye. For example, when glucose is used as the substrate and glucose oxidase as the enzyme label, the colorimetric indicator composition can include a coupler and an oxidizable compound which react to provide a dye. Alternatively, the composition can include a leuco dye and peroxidase or another suitable peroxidative compound which generates a detectable dye as a result of the formation of hydrogen peroxide produced when glucose oxidase converts glucose to gluconic acid. Useful leuco dyes are known in the art and include those, for example, described in U.S. Pat. No. 4,089,747 (issued May 16, 1978 to Bruschi) and U.S. Pat. No. 4,670,385 (issued Jun. 2, 1987 to Babb et al). The particular amounts of the colorimetric indicator composition and its various components are within the skill of a worker in the art.

The labeled ligands can be prepared using known starting materials and procedures, or obtained commercially. Generally, the ligand is attached to the label (e.g. an enzyme moiety) through a covalent bond.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 μL. The finite area which is contacted is generally no more than about 150 mm$^2$.

The amount of ligand is determined by passing the element through a suitable apparatus for detecting the complexed ligand analog directly or the detectable species formed as a result of enzymatic reaction of an enzyme label and a substrate. For example, the species can be detected with suitable spectrophotometric apparatus using generally known procedures. In an enzymatic reaction, the resulting product is determined by measuring, for example, the rate of change of reflection or transmission density in the finite area which was contacted with the test sample. The area which is measured is generally from about 5 to about 25 mm$^2$. The amount of ligand in the liquid sample is inversely proportional to the amount of label measured in the finite area. Generally, label measurement is made after application of a substrate solution.

The layers forming the elements used in the following examples were prepared using the following procedure. Each layer was dried before it was overcoated with another layer.

1. Coating the a cross-linked gelatin layer on subbed poly(ethylene terephthalate) support. The coating composition contained gelatin and an electron transfer agent [e.g., 4'-hydroxyacetanilide (4'-HA)], a buffer, surfactant, and a gelatin hardener.

2. Coating the receptor zone. The coating composition for the zone contains an antibody for the analyte (ligand) immobilized on 0.1–5 μm polymer beads in a polymer according to the invention. In some examples the zone includes a dye, buffer and surfactant.

3. Coating the bead spreading layer over the dried receptor zone. The coating composition contained large (20–35 μm) polymer particles or beads [typically poly(vinyltoluene-co-methacrylic acid) (weight ratio 98/2) beads] adhered together with a latex polymer adhesive, preferably poly(methyl acrylate-co-sodium 2-acrylamido-2-methylpropanesulfonate-co-2-acetoacetoxyethyl methacrylate) (weight ratio 90/4/6). The layer may include a leuco dye, an electron transfer agent, dimedone, a buffer, bovine serum albumin, and a surfactant.

4. A horseradish peroxidase, usually amine-enriched horseradish peroxidase, labeled analyte composition is gravure coated on top of the bead spreading layer. The composition optionally can include an electron transfer agent (4'-HA), a buffer (MOPS), bovine serum albumin, and a hydrophilic polymer vehicle such as polyacrylamide.

A typical element of this invention is presented below. It will be understood by those skilled in the art that the principle of the present invention can be usefully incorporated into any immunoassay element.

| TYPICAL IMMUNOASSAY ELEMENT OF THE INVENTION | Dry Coverage (g/m$^2$) |
|---|---|
| Labeled Ligand Layer (a) | |
| digoxin-HRP | 0.000016 |
| MOPS, pH 7.0 | 0.0045 |
| Bovine serum albumin | 0.000215 |
| Polyacrylamide | 0.00108 |
| 4'-Hydroxyacetanilide | 0.000325 |
| Bead Spreading Layer (b) | |
| TES, pH 7.0 | 0.219 |
| Dimedone | 0.5 |
| Triarylimidazole leuco dye | 0.2 |
| Dimethyl sulfoxide | 1.8 |
| Poly(methyl acrylate-co-sodium 2-acrylamido-2-methylpropanesulfonate-co-2-acetoacetoxyethyl methacrylate) adhesive | 2.583 |
| Bovine serum albumin | 0.5 |
| Poly(m- & p vinyltoluene-co-methacrylic acid) Beads (30 μm) | 130 |
| Zonyl FSN | 0.054 |
| 4'-hydroxyacetanilide | 0.15 |
| Receptor Zone | |
| Triton TX-100 | 0.02 |
| TES, pH 7.0 | 0.1 |
| Antidigoxin beads (1 μm) | 0.015 |
| polymer | 1.0 |
| Cross-linked Gelatin Layer (c) | |
| gelatin | 10 |
| 4'-Hydroxyacetanilide | 0.15 |
| TES, pH 7.0 | 4.58 |
| Triton TX-100 | 0.02 |
| BVSME (hardener) | 0.15 |
| ///////// Poly(ethylene terephthalate) Support ////// | |

This element shows a receptor zone containing antidigoxin antibodies immobilized on 1 μm beads dispersed in polymer. The immobilized receptor was coated with the polymer shown. However, according to the present invention, there may be essentially no polymer in the receptor zone of the finished element. Some, none or essentially all of the polymer will migrate into bead spreading layer (b).

The elements can be used to quantify ligands other than digoxin as stated hereinbefore. The selected labeled ligand depends upon the particular assay. Only one such labeled ligand is used in a single assay with a paired antibody in the receptor zone so that a specific antibody-ligand pair exists for each assay.

The names and symbols used in the above and following elements and following examples have the following meanings:

MOPS: 3-Morpholinopropanesulfonic acid buffer

TES: N-[tris(hydroxymethyl)methyl]-2-aminoethanesulfonic acid

Dimedone: 5,5-Dimethyl-1,3-cyclohexanedione

Triarylimidazole leuco dye: 4,5-Bis(4-dimethylaminophenyl)-2-(4-hydroxy-3,5-dimethoxyphenyl)imidazole blue-forming leuco dye.

Magenta Dye: 4,5-dihydroxy-3-(6,8-disulfo-2-napthylazo)-2,7-naphthalenedisulfonic acid, sodium salt.

HRP: Horseradish peroxidase

BVSME: Bis(vinylsulfonylmethyl) ether gelatin hardener.

PVP-K15: Poly-N-vinylpyrrolidone with an average MW of about 10,000.

PVP-K30: same as PVP-K15 with an average MW of 40,000.

PVP-K90: same as PVP-K15 with an average MW of 360,000.

BSA: Bovine serum albumin.

Zonyl FSN: A nonionic, fluorinated surfactant sold by E. I. du Pont de Nemours.

Antidigoxin beads: Poly[styrene-co-3-(p-vinylbenzylthio)propionic acid] molar ratio 97.6/2.4, weight ratio 95/5 having antidigoxin antibody covalently bound thereto.

PVA: poly(vinyl alcohol)

TX-100: Triton X-100, an octylphenoxy polyethoxy ethanol nonionic surfactant sold by Rohm and Haas.

The following examples 1–4 demonstrate the utility of polymer (I). Examples 5–11 illustrate the utility of polymers (II), (III), (IV), (V), and (VI)

EXAMPLE 1

This example demonstrates that the polymeric polymers used to coat the receptor zone has minimum adverse affect on the binding activity of an antibody receptor.

Digoxin antibodies and horseradish peroxidase labeled digoxin (dgxn-hrp) were used to illustrate the invention.

Comparison assays were carried out on two identical elements using the same polymer to coat the antibody receptor zone. The first element in the comparison had a structure according to the typical element presented hereinbefore except the labeled ligand, horseradish peroxidase-digoxin, was coated over the bead spread layer (b) according to the present invention. The second element in the comparison was identical except it was free of the coated labeled ligand layer (a). The assay was carried out on the first element by simply spotting either 0 or 6 ng/mL of digoxin only. The assay was carried out on the second element by spotting the labeled ligand concurrently with either 0 or 6 ng/mL of digoxin. The elements were then incubated at 37 degrees for 5 minutes. The elements were then removed from the incubator and washed with 10 μL of a wash fluid containing 0.03% hydrogen peroxide. Thereafter the elements were placed in an incubator at 37 degrees, and the rate of leuco dye oxidation was measured.

The difference in the rate measured by change in transmission density/minute (Dt per minute or delta rate) between the high and low concentration of digoxin was used as a measure of sensitivity. Dt is determined by measuring reflectance density which is converted to transmission using the well known Clapper-Williams transform. When the sensitivity for assays carried out on both elements is similar, no prebinding has occurred in the element of the invention.

For further comparison and to show the effects of prebinding in the absence of a separate receptor zone coated with a polymer according to the invention, Table 1 also includes the results obtained with analytical elements in which the antibody receptor is in the bead spreading layer (b). Note that the data shows significant prebinding with gravure coated labeled ligand.

TABLE 1

| Receptor Zone Coating Polymer | Coating Coverage (g/m$^2$) | Spotted or Gravure Coated Label | Rate ΔD$_t$/min |
|---|---|---|---|
| No receptor zone [antibody in the bead spreading layer (b)] | — | spotted gravure | 0.049 0.037 |
| Poly(N-isopropylacryl-amide-co-methacrylic acid-co-N,N'-methylene-bisacrylamide (weight ratio 80/10/10) | 1.0 | spotted gravure | 0.030 0.029 |

This comparison shows that when the receptor zone was coated with a polymer in Table 1 the element of the invention experienced no prebinding and the antibody receptors exhibited good binding activity.

Other polymers tested in the receptor zone according to the above tests provided surprisingly adverse affects on the antibody receptor. Gelatin destroyed the antibody binding capacity completely. With poly(methyl acrylate-co-sodium 2-acrylamido-2-methylpropanesulfonate-co-2-acetoacetoxyethyl methacrylate) the antibody exhibited a delta rate that was too low for use in the receptor zone of an immunoassay element. The latter polymer is disclosed in U.S. Pat. No. 4,258,001. Poly(acrylamide) was also unacceptable. Coating without a polymer resulted in antibody receptors having no binding capacity. Polymers used as adhesives in the bead spreading layer (c), and disclosed in U.S. Pat. No. 4,258,001 by Pierce et al are not useful because they are hydrophobic, non-water-swellable latex particles that coalesce to insoluble films that are barriers to the necessary migration of reagents in the assay process.

EXAMPLE 2

This example demonstrates the superior coating uniformity achieved in the receptor zone with the Group I polymers.

A series of 11 analytical elements were prepared by extrusion hopper coating wherein each layer or zone of the element was dried before coating the next layer. The elements were prepared using poly(N-isopropylacrylamide-co-methacrylic acid-co-N,N'-methylenebisacrylamide) (weight ratio 80/10/10), as the receptor zone polymer according to the invention.

A measure of "uniformity" is the "ΔD$_t$ rate imprecision". The lower the standard deviation (sd) of the rate, the better the layer uniformity. The pooled standard deviation of the above-mentioned elements were determined as follows. Each of the receptor zones were assembled separately into the following dry analytical element.

| | Dry Coverage (g/m²) |
|---|---|
| Labeled Ligand Layer (a) | |
| digoxin-HRP | 0.000016 |
| MOPS, pH 7.0 | 0.0045 |
| Bovine serum albumin | 0.000215 |
| Polyacrylamide | 0.00108 |
| 4'-Hydroxyacetanilide | 0.000325 |
| magenta dye | 0.269 |
| Bead Spreading Layer (b) | |
| TES, pH 7.0 | 0.219 |
| Dimedone | 0.5 |
| Triarylimidazole leuco dye | 0.2 |
| Dimethyl sulfoxide | 1.8 |
| Poly(methyl acrylate-co-sodium 2-acrylamido-2-methylpropanesulfonate-co-2-acetoacetoxyethyl methacrylate) adhesive | 2.583 |
| Bovine serum albumin | 1.0 |
| Poly(m- & p vinyltoluene-co-methacrylic acid) Beads (30 μm) | 130 |
| glycerol | 2.0 |
| 4'-hydroxyacetanilide | 0.45 |
| mannitol | 1.0 |
| Receptor Zone | |
| Triton TX-100 | 0.02 |
| TES, pH 7.0 | 0.1 |
| Antidigoxin beads (0.5 μm) | 0.015 |
| Receptor zone polymer | 0.7 |
| Cross-linked Gelatin Layer (c) | |
| gelatin | 10 |
| 4'-Hydroxyacetanilide | 0.15 |
| TES, pH 7.0 | 4.58 |
| Triton TX-100 | 0.02 |
| BVSME (hardener) | 0.15 |

Each element was spotted with 11 μL of either 0.05 ng/mL or 3.1 ng/mL digoxin in a human serum-based fluid, then placed in an incubator at 37° C. for 5 minutes. The elements were then removed from the incubator and washed with 12 μL of a fluid containing hydrogen peroxide. The elements were placed back into the incubator, and the rate of color formation in the center of the slide was determined using reflectance densitometry as described in example 1. For each receptor zone, 10 elements were analyzed with each fluid. The individual rate sd's were pooled using conventional statistical methods and the statistical significance of the ratio of the variances tested using the F test described in *Statistics for Experimenters, An Introduction to Design, Data Analysis, and Model Building* by Hunter et al., John Wiley & Sons N.Y., N.Y. (1978).

| Receptor Zone Polymer | g/m² | Melt Viscosity (low shear) | Pooled ΔD,/min sd | No. of Coatings |
|---|---|---|---|---|
| Group I Copolymer | 0.7 | * | 0.00192 | 11 |

*The polymers of group (I) used in this invention undergo shear thinning at lower shear rates than most polymer melts and many polymer solutions. The viscosity of a 2.5% solution of the ionic polymer used in this invention at a pH 7 will drop from above about 200 poise or more at 25° C. to about 20 poise or less as shear rate increases, with over 60%, generally over 90%, of the viscosity drop occurring at a shear rate less than about $10^2$/sec. The nonionic polymers exhibit similar behavior at higher concentrations i.e. above about 7%. Because of this viscosity change with changing shear rate, accurate viscosities are difficult to measure, and profiles of viscosity vs shear rate are generally provided instead. Most polymer melts and solutions do not exhibit shear thinning until the shear rate is above about $10^2$/sec to $10^3$/sec.

The data show that the Group I polymers used to coat the immobilized receptors have a low $\Delta D_r$ rate imprecision. Thus greater coating uniformity is achieved with some other polymers according to the invention.

After the uniformly coated layers have been formed higher viscosities are exhibited immediately after coating. This results in a "set" layer that remains stable and uniform during wet transport and drying. Typically, a viscosity at zero shear of over 90 cps is desired to facilitate transport and drying of wet coated layers, while a viscosity of 3–80 cps or less is desired for uniform extrusion hopper coating. The polymers of the invention do not degrade the binding activity of the antibody.

EXAMPLE 3

Analytical elements were prepared for the analytical determination of digoxin having the following format and composition:

DIGOXIN ASSAY ELEMENT

| Component | Dry Coverage (g/m²) |
|---|---|
| Labeled Ligand Layer (a) | |
| Digoxin-HRP | 0.000006 |
| MOPS, pH 7.0 | 0.0045 |
| Bovine Serum Albumin | 0.000215 |
| Polyacrylamide | 0.00108 |
| 3', 5'-Dichloro-4'-hydroxy-acetanilide | 0.00995 |
| 4,5-Dihydroxy-3-(6,8-disulfo-2-naphthylazo)-2,7-naphthalenedisulfonic acid, sodium salt | 0.0538 |
| Triton TX-100 | 0.0043 |
| Bead Spreading Layer (c) | |
| TES, pH 7.0 | 0.219 |
| 3',5'-Dichloro-4'-hydroxy-acetanilide | 0.22 |
| Dimedone | 0.45 |
| Triarylimidazole Leuco Dye | 0.20 |
| Poly(methyl acrylate-co-sodium 2-acrylamido-2-methylpropanesulfonate-co-2-acetoacetoxyethyl methacrylate) Adhesive | 2.583 |
| Poly(m-&p-vinyltoluene-co-methacrylic acid) Beads | 130 |
| Bovine Serum Albumin | 1.0 |
| Glycerol | 2.0 |
| Mannitol | 1.0 |
| Vanadyl Sulfate | 0.04 |
| Receptor Zone | |
| TES | 0.10 |
| TX-100 | 0.02 |
| Antidigoxin Beads (1 μm) | 0.015 |
| Poly(N-isopropylacrylamide-co-sodium 2-acrylamido-2-methylpropanesulfonate-co- | 0.80 |

-continued

DIGOXIN ASSAY ELEMENT

| Component | Dry Coverage (g/m²) |
|---|---|
| N,N'-methylenebisacrylamide) (weight ratio 80/10/10) Cross-linked Gelatin Layer (c) | |
| Gelatin | 10.00 |
| TES | 4.58 |
| 3',5'-Dichloro-4'-hydroxy- acetanilide | 0.44 |
| TX-100 | 0.02 |
| Bis(vinylsulfonylmethyl) ether | 0.15 |
| Poly(ethylene terephthalate) Support | |

Control elements of the same formulation were prepared having no receptor zone. The antidigoxin beads were coated at the same coverage in the bead spreading layer (b).

Both sets of elements were evaluated by the following protocol:

1. Spotted with samples (11 μL) containing either 0.45 ng/mL or 4.0 ng/mL of digoxin,
2. Incubated 5 minutes at 37° C.,
3. Washed with 12 μL of a solution comprising:

| | |
|---|---|
| Hydrogen peroxide | 0.04% |
| 4'-Hydroxyacetanilide | 5 mM |
| N-Cetylpyridinium Chloride | 0.1% |
| Diethylenetriaminepentaacetic Acid | 10 μM |
| Sodium Phosphate Buffer, pH 6.8 | 10 mM |

4. Reading the rate of leuco dye formation at 670 nm. The test results are:

| | Rate Amount of Digoxin (ng/mL) | | |
|---|---|---|---|
| | 0.45 | 4.0 | Rate Range |
| Example 3 | 0.1672 | 0.0757 | 0.0915 |
| Control | 0.1402 | 0.0630 | 0.0772 |

These data show that the element of the invention, including the polymer used to facilitate coating of the bead-antibody receptor particles, has a wider rate range than the control. These results show that the element of this example has greater sensitivity than the control.

EXAMPLE 4

Analytical elements were prepared for the analytical determination of thyroxine (T4) having the same format as described in Example 3 for digoxin with the following changes:
Labeled Ligand Layer (a): Thyroxine-HRP was substituted for Digoxin-HRP and was coated at 0.000016 g/m².
Bead Spreading Layer (b): Bovine gamma globulin replaced bovine serum albumin (coated at 1.0 g/m²).
Leuco dye dispersion was not coated in this layer.
Receptor Zone: Antithyroxine beads replace antidigoxin beads (coated at 0.10 g/m² of 1 μm diameter beads).
The leuco dye dispersion was coated in this zone at the same coverage as in the bead spreading layer of example 3. The presence of polymer in this zone is as described in example 3 for the finshed element.

Cross-linked Layer (c): Furosemide was coated at 0.165 g/m² in addition to all the other ingredients.

This element and a control without the receptor zone but with the leuco dye and the antithyroxine beads coated in the bead spreading layer (b) were compared according to the protocol of example 3 with samples of (11 μL) of human serum spiked with either 0.20 μg/dL or 30 μg/dL T4.

The test results are:

| | Rate Amount of Thyroxine (μg/dL) | | |
|---|---|---|---|
| | 0.20 | 30 | Rate Range |
| Example 4 | 0.2204 | 0.0760 | 0.1444 |
| Control | 0.1845 | 0.0847 | 0.0998 |

The results of this example show that elements according to the invention had a wide rate range compared to the control. This means better sensitivity.

A typical element of this invention used in the following examples 5–14 is presented below. It will be understood by those skilled in the art that the principle of the present invention can be usefully incorporated into any immunoassay element.

Typical Immunoassay Element of the Invention

| Component | Dry Coverage (g/M²) |
|---|---|
| Labeled Ligand Coating | |
| digoxin-HRP | .000016 |
| MOPS, pH 7.0 | .0045 |
| Bovine serum albumin | .000215 |
| Polyacrylamide | .00108 |
| 4'-Hydroxyacetanilde | .000325 |
| Bead Spreading Layer (BSL) | |
| TES, pH 7.0 | .219 |
| Dimedone | 0.5 |
| Triarylimidazole leuco dye | .2 |
| Dimethyl sulfoxide | 1.8 |
| Poly(methyl acrylate-co-sodium 2-acrylamido-2-methylpropanesulfonate-co-2-acetoacetoxyethyl methacrylate) adhesive | 2.583 |
| Bovine serum albumin | 0.5 |
| Poly(m-& p vinyltoluene-co-methacrylic acid) Beads | 130 |
| ZONYL ® FSN | .054 |
| Methanol | .675 |
| 4'-hydroxyacetanilide | |
| Receptor Zone | |
| TRITON ® TX-100 | 0.02 |
| TES.pH 7.0 | 0.1 |
| Antidigoxin beads (1 μm) | 0.015 |
| Polymer | 1.0 |
| Gelatin Layer | |
| gelatin | 10 |
| 4'-Hydroxyacetanilide | .15 |
| TES, pH 7.0 | 4.58 |
| TRITON ® TX-100 | .02 |
| BVSME (hardener) | .15 |

The names and symbols used in the above element and the following examples have the meanings mentioned herein before.

EXAMPLES 5-6

A series of comparison examples were carried out to determine the effect that changes in the polymer in the antibody receptor zone have on the binding activity of the antibody and on prebinding between the antibody and the labeled ligand. Digoxin antibodies and horseradish peroxidase labeled digoxin (dgxn-hrp) are used to illustrate the invention.

In each comparison a different polymer in the receptor zone was used. In each comparison two immunoassays were carried out on two identical elements having the same polymer in the antibody receptor zone. The first element in the comparison had a structure according to the typical element presented hereinbefore except the labeled ligand, horseradish peroxidasedigoxin, was coated over the bead spread layer according to the present invention. The second element in the comparison was identical except it was free of the coated labeled ligand. The assay was carried out on the first element by simply spotting either 0 or 6 ng/mL of digoxin only. The assay was carried out on the second element by spotting the labeled ligand concurrently with either 0 or 6 ng/mL of digoxin. The elements were then incubated at 37 degrees for 5 minutes. The elements were then removed from the incubator and washed with 10 μL of a wash fluid containing 0.03% hydrogen peroxide. The elements were then placed in an incubator at 37 degrees, and the rate of leuco dye oxidation was measured.

The difference in the rate measured by change in transmission density/minute (ΔDt per minute or delta rate) between the high and low concentration of digoxin was used as a measure of sensitivity. Dt is determined by measuring reflectance density which is converted to transmission using the well known Clapper-Williams transform. When the sensitivity for assays carried out on both elements is similar, no prebinding has occurred in the element of the invention.

TABLE 2

| Receptor Zone Polymer | Coverage (g/m²) | Spotted or Gravure Coated Label | Rate ΔD/min |
|---|---|---|---|
| No Receptor Zone | — | spotted | 0.049 |
| | | coated | 0.037 |
| Poly(acrylamide-co-N-vinylpyrrolidone) weight ratio 50/50). | 1.0 | spotted | 0.032 |
| | | Gravure | .030 |
| Poly(acrylamide-co-1-vinylimidazole) | 1.0 | spotted | .032 |
| | | gravure | .028 |

These comparisons show that with the receptor zone polymers in Table 2 the elements of the invention experienced no prebinding and the antibody receptors exhibited good binding activity.

EXAMPLES 7-14

Assays were carried out as in examples 5-6 on the same element except the element did not include a gravure coated labeled ligand. These assays were carried out to identify polymers that did not adversely affect the binding activity of the antibody receptor in the receptor zone. The dry coverage of the polymers in the receptor zone were uniformly 1 g/m². The results presented in Table 3 below compare the polymers to controls in which the antibody is covalently bound to beads in the bead spreading layer and labeled ligand was spotted.

TABLE 3

| Receptor zone polymer | Delta rate |
|---|---|
| Control | .054 |
| Poly(vinyl alcohol) | 0.021 |
| Poly(vinylpyrrolidone) MW 10,000 | .024 |
| Poly(vinylpyrrolidone) MW 40,000 | .045 |
| Control | .051 |
| Poly(vinylpyrrolidone) MW 360,000 | .037 |
| Control | .046 |
| Bovine Serum Albumin | .046 |
| Acacia Gum | .038 |

Each of the polymers in Table 3 did not adversely affect the antibody receptor binding capacity enough to prevent use in a receptor zone in an immunoassay element. Given the absence of prebinding in examples 5-6 in immunoassay elements having a gravure coated labeled ligand one skilled in the art would expect the similar results for the receptor polymers of Table 3.

Other polymers tested in the receptor zone according to the above tests provided surprisingly adverse affects on the antibody receptor. Gelatin destroyed the antibody binding capacity completely. Where poly(methyl acrylate-co-sodium 2-acrylamido-2-methylpropanesulfonate-co-2-acetoacetoxyethyl methacrylate) was used the antibody exhibited a delta rate that was too low for use in the receptor zone of an immunoassay element. This polymer was taken from U.S. Pat. No. 4,258,001 (Pierce et al). Poly (acrylamide) was also unacceptable. Coating without a polymer according to the invention resulted in antibody receptors having no binding capacity.

EXAMPLE 16

An analytical element was prepared for the analytical determination of thyroxine having the following format and composition:

Thyroxine Assay Element

| Component | Dry coverage g/m² |
|---|---|
| Labeled Ligand Layer | |
| Thyroxine-HRP | 0.000016 |
| MOPS, pH 7.0 | 0.0045 |
| Bovine Serum Albumin | 0.000215 |
| Polyacrylamide | 0.00108 |
| 3',5'-Dichloro-4'-hydroxyacetanilide | 0.00995 |
| 4,5-Dihydroxy-3-(6,8-disulfo-2-naphthylazo)-2,7-naphthalenedisulfonic acid, sodium salt | 0.0538 |
| Triton TX-100 | 0.0043 |
| Bead Spreading Layer | |
| TES, pH 7.0 | 0.219 |
| 3',5'-Dichloro-4'-hydroxyacetanilide | 0.22 |
| Dimedone | 0.45 |
| Poly(methyl acrylate-co-sodium 2-acrylamido-2-methylpropanesulfonate-co-2-acetoacetoxyethyl methacrylate) Adhesive | 2.583 |
| Poly(m-& p-vinyltoluene-co-methacrylic acid) Beads | 130 |

-continued

Thyroxine Assay Element

| Component | Dry coverage g/m² |
|---|---|
| Bovine Gamma Globulin | 1.0 |
| Glycerol | 2.0 |
| Mannitol | 1.0 |
| Vanadyl Sulfate | 0.04 |
| Receptor Zone | |
| TES | 0.10 |
| TX-100 | 0.02 |
| Antithyroxine Beads (1 μm) | 0.0.10 |
| Triarylimidazole Leuco Dye | 0.20 |
| Poly(N-ispropylacrylamide-co-sodium 2-acrylamido-2-methyl-propanesulfonate) (weight ratio 85/15) | 0.80 |
| Gelatin Layer | |
| Gelatin | 10.00 |
| TES | 4.58 |
| 3',5'-Dichloro-4'-hydroxyacetanilide | 0.44 |
| TX-100 | 0.02 |
| Furosemide | 0.165 |
| Bis(vinylsulfonylmethyl) ether | 0.15 |
| Poly(ethylene terephthalate) Support | |

Control elements of the same formulation with the receptor beads and leuco dye dispersion in the bead spreading layer were also prepared. Both sets of elements were evaluated by the following protocol:

1. The elements were spotted with samples (11 μL) containing either 0.20 or 30 μg/dL of thyroxine.
2. Incubating the spotted elements 5 minutes at 37° C.,
3. Washing the with 12 μL of a solution containing:

| | |
|---|---|
| Hydrogen peroxide | 0.04% |
| 4'-Hydroxyacetanilide | 5 mM |
| N-Cetylpyridinium Chloride | 0.1% |
| Diethylenetriaminepentaacetic Acid | 10 μM |
| Sodium Phosphate Buffer, pH 6.8 | 10 mM |

4. Reading the rate of leuco dye formation at 670 nm. The test results were:

| | Rate Amount of Thyroxine (μg/dL) | | |
|---|---|---|---|
| | 0.20 | 30 | Rate Range |
| Example 16 | 0.2309 | 0.0720 | 0.1589 |
| Control | 0.1845 | 0.0847 | 0.0998 |

These results show that the elements of the example exhibit a wider rate range compared to the control. This translates to better sensitivity.

The invention has been described in detail with particular reference to preferred embodiments thereof, but it will be understood that variations and modifications can be effected within the spirit and scope of the invention.

We claim:

1. A dry immunoassay analytical element for assaying a ligand comprising, in the following order, (a) a layer containing a labeled ligand, (b) a bead spreading layer, (c) a cross-linked hydrophilic polymer layer and (d) a support; wherein (i) a fixed concentration of an immobilized receptor for the labeled ligand is located in a receptor zone under layer (b) and over layer (c) wherein the receptor zone is coated with a polymer selected from the group consisting of (I), (II), (III), (IV), (V) and (VI) as follows:

(I) cross-linked polymers comprising about 30 to 97 weight percent of polymerized N-alkyl-substituted acrylamide monomers, about 3 to 25 weight percent polymerized crosslinking monomer having at least two addition polymerizable groups per molecule of crosslinking monomer, and 0 to 60 weight percent of other polymerized hydrophilic monomers (II) poly (vinyl alcohol);

(III) bovine serum albumin;

(IV) acacia gum;

(V) homopolymers of poly-N-vinylpyrrolidone having a molecular weight in the range 8000, to 400,000; and (VI) water-soluble vinyl addition copolymers having two or more monomers selected from the group consisting of acrylamide, methacrylamide, N-alkyl-substituted acrylamides, N-alkyl substituted methacrylamides, 1-vinylimidazole, 2-alkyl substituted-1-vinylimidazoles, 2-hydroxyalkyl substituted-1-vinylimidazoles, N-vinylpyrrolidone, hydroxyalkyl acrylates, hydroxyalkyl methacrylates, acrylic acid, sulfoalkyl acrylates, sulfatoalkyl acrylates, sulfoalkyl methacrylates, sulfatoalkyl methacrylates, N-sulfoalkylacrylamides, N-sulfatoalkylacrylamides, and N-sulfoalkylmethacrylamides, N-sulfatoalkylmethacrylamides, ethylenesulfonic acid and sulfo-substituted styrenes; and (ii) the receptors are immobilized by being covalently bonded to polymeric beads that are smaller than the beads in layer (b), said receptor zone being coated with a polymer.

2. The element of claim 1 wherein the receptor zone is coated with polymer (I) and wherein the N-alkyl substituted acrylamide of polymer (I) is present in an amount of 60 to 97 weight percent and is selected from the group consisting of N-isopropylacrylamide, N-n-butylacrylamide, N,N-diethylacrylamide and N-n-propylacrylamide.

3. The element of claim 2 wherein the N-alkyl substituted acrylamide is N-isopropylacrylamide.

4. The element of claim 1 and wherein the receptor zone is coated with polymer (I) and wherein the crosslinking monomer in polymer (i) is N,N'-methylenebisacrylamide.

5. The element of claim 1 wherein the receptor zone is coated with polymer (VI) and wherein the hydrophilic monomer in polymer (I) is 5 to 35 weight percent of the polymer.

6. The element of claim 1 wherein the receptor zone is coated with polymer (VI) and wherein the polymer is selected from the group consisting of poly(N-isopropylacrylamide-co-methacrylic acid-co-N,N'-methylenebisacrylamide); poly(N-isopropylacrylamide-co-sodium 2-acrylamido-2-methylpropanesulfonate-co-N,Nlmethylenebisacrylamide) (weight ratio 80/10/10); poly(N-isopropylacrylamide-co-2-hydroxyethyl methacrylate-co-N,N'-methylenebisacrylamide) (85/5/10); poly(N-isopropylacrylamide-co-2-hydroxyethyl methacrylate-co-sodium 2-acrylamido-2-methylpropanesulfonate-co-N, N'methylenebisacrylamide) (80/5/5/10); poly(N-isopropylacrylamide-co-2-hydroxyethyl methacrylate-co-sodium 2-acrylamido-2-methylpropanesulfonate-co-N,N'- methylenebisacrylamide) (83/5/2.5/9.5); poly(N-isopropylacrylamide-co-2-hydroxyethyl methacrylate-co-sodium 2-acrylamido-2-methylpropanesulfonate-co-N,N'-methylenebisacrylamide) (84.5/5/0.5/10); poly(N-isopropylacrylamide-co-2-hydroxyethyl methacrylate-co-sodium 2-acrylamido-2-methylpropanesulfonate-co-N,N'-methylenebisacrylamide) (83/5/2/10); and poly(N-isopropylacrylamide-co-2-hydroxyethyl methacrylate-co-sodium 2-acrylamido-2-methylpropanesulfonate-co-N,N'-methylenebisacrylamide) (80.9/4.8/4.8/9.5).

7. The element of claim 1 wherein the monomers forming the water-soluble vinyl addition copolymers (VI) are selected from the group consisting of 2-acrylamido-2-methylpropanesulfonic acid, sodium salt; o- and p-styrenesulfonic acid, potassium salt; p-styrenesulfonic acid, potassium salt; p-styrenesulfonic acid, sodium salt; ethylenesulfonic acid, sodium salt 2-Sulfoethyl methacrylate, sodium salt; 2-sulfoethyl methacrylate; 3-acryloyloxypropane-1-sulfonic acid, sodium salt, 3-methacryloyloxypropane-1-sulfonic acid, sodium salt; 3-sulfobutyl methacrylate, sodium salt; 4-sulfobutyl methacrylate, sodium salt; N-(2-sulfo-1,1-dimethylethyl) acrylamide, potassium salt; and sodium 2-methacryloyloxyethylsulfate.

8. The element of claim 1 wherein the polymer used to coat the receptor zone is selected from the group consisting of poly-N-vinylpyrrolidone having a molecular weight in the range 10,000 to 360,000, bovine serum albumin, acacia gum, poly(acrylamide-co-N-vinylpyrrolidone), poly (acrylamide-co-1-vinylimidazole), and poly(vinyl alcohol).

9. The element of claim 6 wherein the polymer is poly (N-isopropylacrylamide-co-sodium 2-acrylamido-2-methylpropanesulfonate) (weight ratio 85/15).

10. The element of claim 9 wherein the ligand comprises a hapten or hapten analog selected from the group consisting of digoxin, phenytoin, carbamazepine, phenobarbital, theophylline and thyroxine.

11. The element of claim 10 wherein the label is horseradish peroxidase; the labeled ligand layer further comprises an electron transfer agent; and the bead spreading layer comprises a leuco dye that changes from colorless to color in the presence of peroxidase and hydrogen peroxide.

12. The element of claim 11 wherein the beads in layer (b) have a diameter of 25–35 μm and the beads upon which the receptors are immobilized have a diameter of 0.1 to 5 μm.

13. An element according to claim 12 wherein layer (c) contains an electron transfer agent, a buffer and the hydrophilic cross-linked polymer is selected from the group consisting of gelatin, poly[acrylamide-co-N-vinylpyrrolidone-co-N-(3-acetoacetamidopropyl) methacrylamide] and poly(acrylamide-co-N-vinylpyrrolidone-co-2-acetoacetoxyethyl methacrylate).

14. An element according to claim 13 wherein the electron transfer agent is 4'-hydroxyacetanilide and the cross-linked polymer is gelatin.

15. The element of any one of the preceding claims wherein the receptor is an antibody for the ligand, the label on the ligand is an enzyme and the labeled ligand is present at a coverage less than, the same as or some multiple of the amount of labeled ligand used when the assay is carried out by contacting the analytical element concurrently with a test sample and labeled ligand.

16. A method for the assay of an immunologically reactive ligand in an aqueous liquid sample, comprising the steps of:

A. providing a dry immunoassay analytical element, for assaying a ligand according to claim 1 wherein the labeled ligand is enzyme labeled;

B. contacting a finite area of the layer comprising the enzyme labeled ligand with a sample of the liquid sample thereby forming at least one of (i) an immobilized ligand-receptor complex and (ii) an immobilized enzyme labeled ligand-receptor complex in the receptor zone;

C. contacting the finite area of the layer comprising the enzyme labeled ligand with a solution of substrate for the ligand thereby catalyzing the development of a color; and D. determining the concentration of the ligand colorimetrically.

* * * * *